United States Patent
Dimmit et al.

(10) Patent No.: US 6,288,276 B1
(45) Date of Patent: *Sep. 11, 2001

(54) SALICYLALDOXIMES AND METHOD OF PREPARATION

(75) Inventors: Jeffrey H. Dimmit, Joplin, MO (US); Mark A. Kearns, Netley (GB); William H. Chambless, Plano, TX (US)

(73) Assignee: Henkel Kommanditgeselschaft auf Aktien, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/561,667

(22) Filed: May 2, 2000

Related U.S. Application Data

(63) Continuation of application No. 09/217,258, filed on Dec. 21, 1998, now abandoned, which is a continuation-in-part of application No. 08/861,135, filed on May 21, 1997, now Pat. No. 5,856,583.

(51) Int. Cl.⁷ .......................... C07C 249/08; C07C 45/00
(52) U.S. Cl. .......................... 564/259; 564/265; 568/433
(58) Field of Search .................................. 568/433, 437, 568/432, 426; 564/265, 259

(56) References Cited

U.S. PATENT DOCUMENTS

| | | | |
|---|---|---|---|
| 5,260,487 | * 11/1993 | Levin | 568/433 |
| 5,354,920 | * 10/1994 | Cox et al. | 568/437 |
| 5,502,254 | * 3/1996 | Levin | 568/259 |

* cited by examiner

*Primary Examiner*—Sreeni Padmanabhan
(74) *Attorney, Agent, or Firm*—John E. Drach; Henry E. Millson, Jr.

(57) ABSTRACT

Process for making Oximes of the formula IV

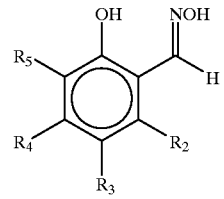

IV wherein each of $R_2$–$R_5$ is hydrogen, a halogen, an alkyl or cycloalkyl group having from 1 to 36 carbon atoms, an aryl or alkaryl group having from 1 to 36 carbon atoms, an alkoxy or an aryloxy group having from 1 to 30 carbon atoms, an acyl group having from 1 to 24 carbon atoms and intermediates leading thereto are described.

42 Claims, No Drawings

SALICYLALDOXIMES AND METHOD OF PREPARATION

CROSS-REFERENCE TO RELATED APPLICATIONS

This application is a CON of U.S. Ser. No. 09/217,258, filed Dec. 21, 1998, now abandoned continuation-in-part of application Ser. No. 08/861,135, filed on May 21, 1997, now U.S. Pat. No. 5,856,583 the entire contents of which are incorporated herein by reference.

STATEMENT REGARDING FEDERALLY SPONSORED RESEARCH OR DEVELOPMENT

Not Applicable.

BACKGROUND OF THE INVENTION

Ortho-formylated phenols and their derivatives are valuable intermediates in the preparation of products for the chemical, pharmaceutical and mining industries. Therefore, processes for making hydroxyarylaldehydes, and in particular, 2-hydroxyarylaldehydes, have been well researched. It is well recognized that such hydroxyarylaldehydes can be made by reacting magnesium phenoxides with formaldehyde under anhydrous conditions.

SUMMARY OF THE INVENTION

The present invention relates to an oxime of the formula IV, a process for making an oxime of the formula IV, an aryloxy magnesium salt of the formula II, a process for making an aryloxy magnesium salt of the formula II and a process for making an aldehyde of the formula III

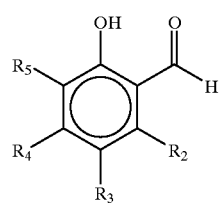

The process for making an oxime of the formula IV

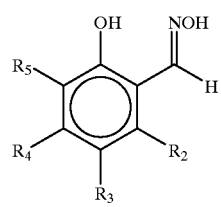

wherein each of $R_2$–$R_5$ is hydrogen, a halogen, an alkyl or cycloalkyl group having from 1 to 36 carbon atoms, an aryl or alkaryl group having from 1 to 36 carbon atoms, an alkoxy or an aryloxy group having from 1 to 30 carbon atoms, an acyl group having from 1 to 24 carbon atoms comprises the steps of: (1) reacting a compound of the formula I

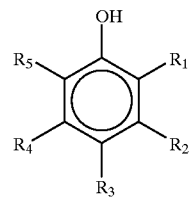

wherein each of $R_1$–$R_5$ is hydrogen, a halogen, an alkyl or cycloalkyl group having from 1 to 36 carbon atoms, an aryl or alkaryl group having from 1 to 36 carbon atoms, an alkoxy or an aryloxy group having from 1 to 30 carbon atoms, an acyl group having from 1 to 24 carbon atoms with the proviso that one of $R_1$–$R_5$ is hydrogen with magnesium alkoxide to form an aryloxy magnesium compound: (2) reacting the aryloxy magnesium compound with a compound capable of forming a non-aryloxy anion X to form a compound of the formula II wherein X is a non-aryloxy anion selected from the group consisting of chloride, acetate, sulfate, nitrate, sulfonate, hydroxide, oxide, carboxylate, formate; N is an integer having a value of 1 or 2; each of $R_1$–$R_5$ is defined as above to form an aryloxy magnesium salt of the formula II;

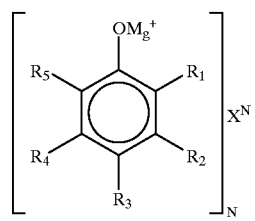

(3) reacting a compound of the formula II with formaldehyde to yield an aldehyde of the formula III

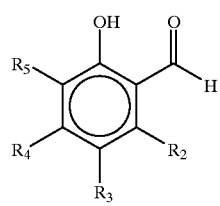

(4) reacting a compound of the formula III with hydroxylamine to produce an oxime of the formula IV.

The process for making an aryloxy magnesium salt of the formula II

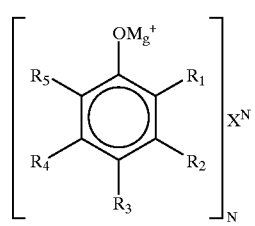

comprises reacting a compound of the formula I

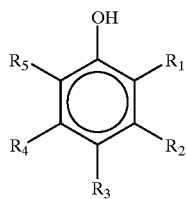

I wherein each of $R_1$–$R_5$ is hydrogen, a halogen, an alkyl or cycloalkyl group having from 1 to 36 carbon atoms, an aryl or alkaryl group having from 1 to 36 carbon atoms, an alkoxy or an aryloxy group having from 1 to 30 carbon atoms, an acyl group having from 1 to 24 carbon atoms with magnesium alkoxide to form an aryloxy magnesium compound; (2) reacting the aryloxy magnesium compound with a compound capable of forming a non-aryloxy anion X wherein X is a non-aryloxy anion selected from the group consisting of chloride, acetate, sulfate, nitrate, sulfonate, hydroxide, oxide, carboxylate, formate; N is an integer having a value of 1 or 2; and each of $R_1$–$R_5$ is defined as above.

The process for making an aldehyde of the formula III comprises (1) reacting a compound of the formula I

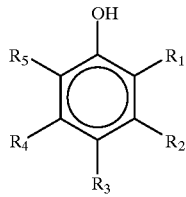

I wherein each of $R_1$–$R_5$ is defined as above with magnesium alkoxide to form an aryloxy magnesium salt of the formula II;

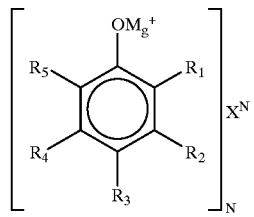

II (2) reacting the aryloxy magnesium compound with a compound capable of forming a non-aryloxy anion X to form a compound of the formula II wherein X is a non-aryloxy anion selected from the group consisting of chloride, acetate, sulfate, nitrate, sulfonate, hydroxide, oxide, carboxylate, formate; N is an integer having a value of 1 or 2; each of $R_1$–$R_5$ is defined as above with the proviso that one of $R_1$ or $R_5$ is hydrogen; (3) reacting a compound of the formula II with formaldehyde to yield an aldehyde of the formula III

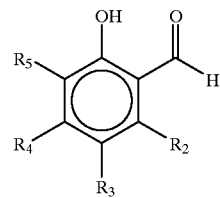

III

Unlike similar methods which employ non-aryloxy anions, step (3) above can be carried out in the presence of water.

BRIEF DESCRIPTION OF THE SEVERAL VIEWS OF THE DRAWING

Not Applicable.

DETAILED DESCRIPTION OF THE INVENTION

The oximes according to the invention are compounds of the formula IV

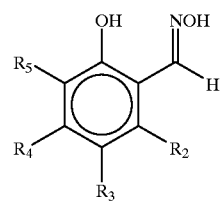

IV wherein each of $R_2$–$R_5$ is hydrogen, a halogen, an alkyl or cycloalkyl group having from 1 to 36 carbon atoms, an aryl or alkaryl group having from 1 to 36 carbon atoms, an alkoxy or an aryloxy group having from 1 to 30 carbon atoms, an acyl group having from 1 to 24 carbon atoms. These compounds, which can be made by the processes disclosed herein, are useful as extractants for metals from aqueous solutions such as from aqueous acid leach solutions in metal recovery operations. The preferred compounds of formula IV are those wherein $R_3$ is a dodecyl group or a nonyl group and each of $R_2$, $R_4$ and $R_5$ is hydrogen.

The aryloxy magnesium salts according to the invention are those of the formula II

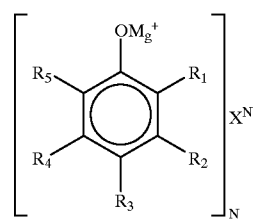

II wherein each of $R_2$–$R_5$ is hydrogen, a halogen, an alkyl or cycloalkyl group having from 1 to 36 carbon atoms, an aryl or alkaryl group having from 1 to 36 carbon atoms, an alkoxy or an aryloxy group having from 1 to 30 carbon atoms, an acyl group having from 1 to 24 carbon atoms. The aryloxy magnesium salts are useful as intermediates in the production of the aldehydes of formula III and the oximes of formula IV as disclosed herein. The preferred aryloxy magnesium salts are those in which $R_3$ is a dodecyl or a nonyl group; $R_3$ is a dodecyl group and each of $R_2$, $R_4$ and $R_5$ hydrogen; $R_3$ is a nonyl group, each of $R_2$, $R_4$ and $R_5$ hydrogen and X is an acetate ion or a chloride ion.

The processes according to the invention begin with the formation of the aryloxy magnesium salt of the formula II. This compound can be made by reacting a phenolic compound of the formula I wherein at least one of the ortho positions, i.e. the 2- and/or 6-positions of the aromatic ring with respect to the carbon carrying the phenolic hydroxyl group, are free. That is, they are bonded to hydrogen. The other four positions in the aromatic nucleus may carry substituents which are inert under the reaction conditions. Suitable examples of such substituents include one or more of hydrogen atoms; halogen atoms; alkyl, cycloalkyl, and alicyclic groups, aryl groups, alkaryl groups, aralkyl groups having 1–36 carbon atoms; alkoxy groups, aryloxy groups which have from 1–30 carbon atoms; acyl groups which have from 1–24 carbon atoms; and any combinations thereof. Such compounds can be prepared by any of the methods known to those skilled in the art.

The aryloxy magnesium salt of the formula II is made from an arlyoxy magnesium intermediate. The arlyoxy magnesium intermediate can be prepared by any of the methods known to those skilled in the art. Such methods include, for example, reacting magnesium in the form of its alkoxide, e.g. methoxide, with a reactant capable of providing the aryloxy group, i.e. a phenolic compound, such as e.g. para-nonyl phenol, in the presence of a non-polar solvent such as e.g. benzene, toluene, xylene or cyclohexane optionally in the presence of a polar co-solvent. Examples of polar cosolvents that may be used include one or more of: lower C1–C4 alcohols such as, e.g., methanol and ethanol; amines such as e.g. triethylamine or pyridine; amides such as, e.g., dimethylformamide and N,N-dimethylacetamide; sulfoxides such as, e.g., dimethyl sulfoxide; mono-glyme, di-glyme and tri-glyme; and ethers such as, e.g., diethyl ether, diphenyl ether and tetrahydrofuran. The reaction mixture is heated to reflux to allow the magnesium to dissolve. The phenolic compound, e.g. nonyl phenol, is then added to this solution of magnesium alkoxide in a non-polar solvent with agitation to ensure good mixing of the reactants. The mixture is suitably heated for a period to facilitate completion of the reaction. The temperature for this step is preferably within the range from 25° C. to the boiling point of the reaction mixture. The reaction is preferably run at or near the boiling point of the solvent used for the reaction. For example, if toluene is used as the solvent and magnesium methoxide is the alkoxide, the reaction mixture is preferably run at a temperature of about 65° C. The duration of the reaction is generally in the range from about 30 minutes to several hours depending upon the reaction temperature employed. In general, lower temperatures which require longer reaction times to complete the conversion. When the reaction is run at or near the boiling point of the solvent system used, a reaction time of 30 to 60 minutes should be sufficient for completion of the conversion. The relative mole ratios of the phenolic compound to the magnesium alkoxide is suitably in the range from about 0.9:1 to about 1.1:1, and is preferably about 1:1. Subsequently, the non-polar solvent and the polar co-solvent are then removed as an azeotrope from the reaction mixture by fractional distillation. The reaction may be carried out at ambient or under reduced pressure, the latter being used to facilitate the removal of volatile by-products of the reaction. The resultant aryloxy magnesium compound is then reacted with a compound capable of providing the desired non aryloxy anion such as e.g. an oxide, a hydroxide, a carboxylate, sulphate or a nitrate anion to form the aryloxy magnesium salt of the formula II. An example of a compound capable of providing a carboxylate anion is glacial acetic acid which provides an acetate anion. The relative mole ratios of the aryloxy magnesium compound to the compound capable of giving rise to the non-aryloxy anion is suitably in the range from about 0.9:1 to about 1.1:1, and is preferably about 1:1. The addition of the compound capable of giving rise to the non-aryloxy anion is suitably carried out over a short duration e.g. from 1 to 3 hours at a temperature in the range from about 60–80° C. and at either ambient or reduced pressure, e.g. about 350 mm Hg. When the addition of the compound providing the non-aryloxy anion is complete, the desired aryloxy magnesium salt is generated and is ready for the next stage of the reaction. In this context, it should be understood that due to the greater affinity of the non-aryloxy anions towards the aryloxy magnesium cation when compared with the alkoxy ligands of prior art, the final aryloxy magnesium salt so formed is substantially free of any aryloxymagnesium alkoxide. The addition of the formaldehyde reactant to the aryloxy magnesium salt can then be commenced. The relative mole ratios of the aryloxy magnesium salt to the (para)formaldehyde for this stage of the reaction is suitably in the range from about 2 to 3.5, preferably from about 2.5 to 3. This stage of the reaction is carried out at a temperature in the range suitably from 40° to 120° C., and preferably from 45–100° C. The formaldehyde may be added as a gas, a solid or as a solution of solid paraformaldehyde in an anhydrous solvent over a duration, e.g., of 1 to 10 hours and during this addition the reaction temperature is suitably in the range of 60–90° C. Whichever form is used, the reaction mixture and the added reactants, with the exception of paraformaldehyde, are substantially anhydrous. During this step of addition of formaldehyde, any volatile reaction by-products formed are removed continually from the reaction mixture by distillation. When the addition of formaldehyde is completed, the reaction temperature is suitably raised to about 70–100° C. and maintained at that temperature for a further duration, e.g., 2–5 hours, preferably about 3 hours. Thereafter, a strong acid solution, such as e.g. a 10% aqueous solution of sulfuric acid, is added to the reaction mixture and stirred for a duration, e.g., 1 hour and the reaction mixture is then allowed to undergo phase separation. Upon separation of the phases, the organic phase is washed several times with water, the organic phase dried and rendered free of any solvents. The residual product is crude 2-hydroxy arylaldehyde. Where para-nonyl phenol is used, the crude product will be 5-nonylsalicylaldehyde. The crude product can be purified by methods known to those skilled in the art such as, e.g., distillation under reduced pressure, especially if the product aldehyde is of a relatively higher molecular weight. The 2-hydroxyarylaldehydes so formed are very useful compounds. They can, for instance, be converted to the corresponding oximes and used as metal extractants. It can also be used in the pharmaceutical industry, in the production of perfumes and agrochemicals. A feature of the present invention is its ability to tolerate the presence of water. For instance, commercial paraformaldehyde solid usually contains up to 7% by weight of water and this can readily be used in the present process. Moreover, the present process allows the use of water as the acidic species in order to generate non-aryloxy anions in the salt such as e.g. oxide or hydroxide. This is a significant point of distinction over prior art processes such as those described in U.S. Pat. Nos. 5,354,920 and 5,260,487, both of which require the use of substantially anhydrous conditions.

The oximes according to the invention can be made from the aldehydes according to the invention by any method known to those skilled in the art. Preferably, the oximes are made by reacting the appropriate aldehyde with hydroxylamine sulfate in an aqueous solution in a pH of from about 7 to about 10, preferably in the range between 7 and 9. The pH adjustment is preferably made using aqueous NaOH. The oximation can be carried out a temperature of from about 25° C. to about 100° C., preferably from about 70° C. to about 75° C. The oxime can be purified by fractional distillation as described in Example 5.

The following are examples which are meant to illustrate but not to limit the invention.

EXAMPLE 1

A 2-liter round-bottomed flask was charged with magnesium (12 g, 0.49 mol), methanol (285 ml), toluene (120 ml) and magnesium methoxide (10 ml solution of 7.4% by weight magnesium methoxide in methanol). The reaction mixture was heated to reflux and the magnesium dissolved. Para-nonyl phenol (112.4 g) was added in one portion to the reaction mixture. The flask was then rigged for a fractional vacuum distillation and an azeotrope of methanol/toluene was distilled off to an internal temperature of 70° C. at a pressure of 350 nun Hg. Glacial acetic acid (28.5 ml, 0.5 mole) was added to the reaction mixture over a 1 hour period while maintaining the reaction temperature at 70° C. and the pressure at 350 mm Hg. When the addition of glacial acetic acid was complete, solid paraformaldehyde (46 g, a commercial sample containing 5–7% by weight water) was added over a 105 minute period. The reaction mixture was maintained at a temperature of 65° C. and a pressure of 350 mm Hg. During the addition of paraformaldehyde and the volatile reaction by-products were continually removed. When the paraformaldehyde addition was complete, the reaction temperature was increased to 75° C. and maintained at that temperature for an additional 3 hours. Sulfuric acid (300 ml, 10% wow) was added to the reaction mixture, which was then stirred for 1 hour. After phase separation, the organic phase was washed twice with 200 ml portions of water. The washed organic phase was then separated, dried and rendered free of the solvent to yield crude-nonyl salicylaldehyde. A 67% yield was obtained.

EXAMPLE 2

A 2-liter round-bottomed flask was charged with magnesium (12 g, 0.49 mol), methanol (285 ml), toluene (120 ml) and magnesium methoxide (10 ml solution of 7.4% by weight magnesium methoxide in methanol). The reaction mixture was heated to reflux and the magnesium dissolved. Para-nonyl phenol (112.4 g) was added in one portion to the reaction mixture. The flask was then rigged for a fractional vacuum distillation and an azeotrope of methanol/toluene was distilled off to an internal temperature of 70° C. at a pressure of 350 mm Hg. Glacial acetic acid (28.5 ml, 0.5 mole) was added to the reaction mixture over a 1 hour period while maintaining the reaction temperature at 70° C. and the pressure at 350 mm Hg. When the addition of glacial acetic acid was complete, pyridine (79 ml) and toluene (250 ml) were added. An azeotrope of methanol and toluene was distilled at a pot temperature of 100° C. The reaction mixture was then cooled to 95° C. and solid paraformaldehyde (46 g, a commercial sample containing 5–7% by weight water) was added over a 45 minute period. The reaction mixture was maintained at a temperature of 95–100° C. during the addition of paraformaldehyde and volatile reaction by-products were continually removed by distillation. When the paraformaldehyde addition was complete, the reaction temperature was maintained at 95–100° C. for an additional 2 hours. Sulfuric acid (300 ml, 10% w/w) was added to the reaction mixture, which was then stirred for 1 hour. After phase separation, the organic phase was washed twice with 200 ml portions of water. The washed organic phase was then separated, dried and rendered free of the solvent to yield crude 5-nonyl salicylaldehyde. A 78% yield was obtained.

EXAMPLE 3

A 2-liter round-bottomed flask was charged with magnesium (24 g, 0.98 mol), methanol (570 ml), toluene (240 ml) and magnesium methoxide (10 ml solution of 7.4% by weight magnesium methoxide in methanol). The reaction mixture was heated to reflux and the magnesium dissolved. Para-nonyl phenol (224 g) was added in one portion to the reaction mixture. The flask was then rigged for a fractional vacuum distillation and an azeotrope of methanol/toluene was distilled off to an internal temperature of 70° C. at a pressure of 350 mm Hg. The mixture was cooled to 25° C. and toluene (300 ml) was added. Anhydrous hydrochloric acid (38 g) was added to the reaction mixture over a period of 1.5 hours. Methanol (200 ml) was then added to the mixture and the pot was rigged for an atmospheric pressure fractional distillation. An azeotrope of methanol/toluene was distilled off to a pot temperature of 100° C. The pot was then cooled to 90° C. and paraformaldehyde (94.8 g, a commercial sample containing 5–7% by weight water) slurried in toluene (200 ml) was added over a 1 hour period. During the addition of paraformaldehyde, volatile reaction by-products were continually removed. The reaction mixture was maintained at a temperature of 90° C. for an additional hour after the paraformaldehyde addition was complete. The reaction temperature was then cooled to 70° C. and sulfuric acid (300 ml, 10% w/w) was added to the reaction mixture, which was then stirred for 30 minutes. After phase separation, the organic phase was washed twice with 200 ml portions of water. The washed organic phase was then separated, dried and rendered free of the solvent to yield crude 5-nonyl salicylaldehyde. A 62% yield was obtained.

EXAMPLE 4

A 2 liter round-bottomed flask was charged with magnesium turnings (12.2 g, 0.50 mole), methanol (13 3 ml), toluene (60 ml), and magnesium methoxide solution (10 ml of an 8 weight % solution of magnesium methoxide in methanol). The reaction mixture was heated to 45° C. at which point the magnesium dissolution became vigorous. The temperature of the reaction mixture was maintained between 45 and 55° C. Para-dodecyl phenol (128.0 g, 0.50 mole) dissolved in toluene (125 ml) was added in one portion to the reaction mixture which was then maintained at 65° C. for one hour. Glacial acetic acid (30.1 g, 0.50 mole) was added over a 1 hour period, while maintaining the reaction mixture at reflux (65–66°). The reaction flask was then rigged for fractional distillation and the methanol/toluene azeotrope was distilled off until an internal temperature of 85° C. A total of 117 g of distillate, assaying 65% methanol and 35% toluene, was collected. Toluene (130 g) was added to the reaction mixture in one portion. Paraformaldehyde (45.0 g) slurried in toluene (90 g) was then added over a 90 minute period. During the addition, the reaction mixture was maintained at a temperature of 85–90° C. allowing a continuous distillation of the volatile reaction by-products. When the paraformaldehyde addition was complete, the reaction mixture was maintained at 90° C. for an additional 90 minutes. The reaction mass was then cooled to 35° C. and 500 ml of 20 vol % sulfuric acid was added. The hydrolysis mass was then stirred for an additional 45 minutes. After phase separation, the organic phase was washed twice with 200 ml portions of water. The washed organic phase was then separated, dried and rendered free of the solvent to yield crude 5-dodecyl salicylaldehyde. A 65% yield was obtained.

EXAMPLE 5

A sample of 2-hydroxy-5-nonylbenzaldehyde (5-nonyl salicylaldehyde) obtained from a preparation similar to that set forth in Examples 1–3 was fractionally distilled prior to use in this example. The 2-hydroxy-5-nonylbenzaldehyde used was a combination of a first fraction boiling at 178° C. and at 17 mm Hg and a second fraction boiling at 175° C. and at 18 mm Hg. Each fraction contained about 87% 2-hydroxy-5-nonylbenzaldehyde as determined by titration with 0.1 N NaOH of the HCL produced by the reaction of the substituted benzaldehyde with excess hydroxylamine hydrochloride.

Into a 500 ml flask equipped with an agitator, a thermometer and a condenser was placed 129.5 grams of 30% aqueous hydroxylamine sulfate and 73.5 grams of 25% aqueous NaOH. The pH was increased from 8.1 to 9.2 by the addition of 25% aqueous NaOH as required. About 100 grams total (50 grams each) of the combined fractions of 2-hydroxy-5-nonylbenzaldehyde described above were added and the entire contents of the flask heated to about 75° C. and held at that temperature for about one hour. About 100 ml of toluene and 100 ml of deionized water were then added, the reaction mass mixed and phase-separated. The organic phase (containing the oxime) was washed twice with 100 ml portions of deionized water and the washed phase stripped under vacuum to remove the toluene and any residual water. A 54 gram portion of the isolated dried 2-hydroxy-5-nonylbenzadloxime was blended with 20 grams of EXAL® 13, a trademark product of Exxon Corp., which is $C_{13}$ alcohol, 26 grams of ESCADE® 100, a trademark product of Exxon Corp., which is a liquid hydrocarbon diluent. A copper extraction performance test was run on this sample and gave the following test results: Extraction Isotherm Point=5.0 g Cu/liter; Break time=30 sec; 99% kinetics; Stripped Organic=1.4 grams Cu/liter; Maximum Load=5.5 grams Cu/liter; Cu/Fe selectivity=7800; Net Cu Transfer=3.6 grams Cu/liter; Degree of Modification=5.0.

What is claimed is:

1. A process for making an oxime of the formula IV

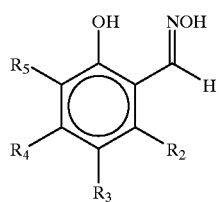

wherein each of $R_2$–$R_5$ is independently hydrogen, a halogen, an alkyl or cycloalkyl group having from 1 to 36 carbon atoms, an aryl or alkaryl group having from 1 to 36 carbon atoms, an alkoxy or an aryloxy group having from 1 to 30 carbon atoms, or an acyl group having from 1 to 24 carbon atoms which comprises the steps of: (1) reacting a compound of the formula I

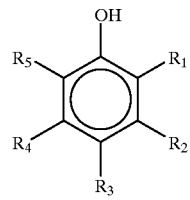

wherein each of $R_1$–$R_5$ is independently hydrogen, a halogen, an alkyl or cycloalkyl group having from 1 to 36 carbon atoms, an aryl or alkaryl group having from 1 to 36 carbon atoms, an alkoxy or an aryloxy group having from 1 to 30 carbon atoms, or an acyl group having from 1 to 24 carbon atoms with the proviso that one of $R_1$ or $R_5$ is hydrogen with magnesium alkoxide to form an aryloxy magnesium compound; (2) reacting the aryloxy magnesium compound with a compound capable of forming a non-aryloxy anion X wherein X is selected from the group consisting of acetate, sulfate, nitrate, sulfonate, hydroxide, oxide, carboxylate and formate; to form an aryloxy magnesium salt of the formula II

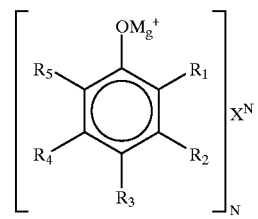

wherein $R_1$–$R_5$, and X are defined as above and N is an integer having a value of 1 or 2; (3) reacting the aryloxy magnesium salt of the formula II with formaldehyde to yield an aldehyde of the formula III

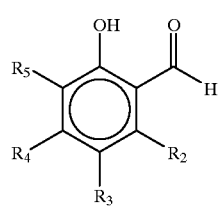

wherein $R_2$–$R_5$ are defined as above; (4) reacting the aldehyde of the formula III with hydroxylamine to produce an oxime of the formula IV.

2. The process of claim 1 wherein in formula I $R_3$ is a dodecyl group.

3. The process of claim 1 wherein in formula I $R_3$ is a nonyl group.

4. The process of claim 1 wherein in formula I $R_3$ is a dodecyl group and each of $R_2$, $R_4$ and $R_5$ is hydrogen.

5. The process of claim 1 wherein in formula I $R_3$ is a nonyl group and each of $R_2$, $R_4$, and $R_5$ is hydrogen.

6. The process of claim 1 wherein in formula II X is an acetate ion.

7. The process of claim 1 wherein step (1) is carried out in the presence of a non polar solvent.

8. The process of claim 7 wherein the non-polar solvent is one or more of the solvents selected from the group consisting of benzene, toluene, xylene and cyclohexane.

9. A process according to claim 7 wherein a polar co-solvent is used in conjunction with the non-polar solvent.

10. A process according to claim 9 wherein the polar co-solvent is selected from the group consisting of methanol, ethanol, triethylamine, pyridine, dimethylformamide, N,N-dimethylacetamide, dimethyl sulfoxide, mono-glyme, di-glyme, tri-glyme, diethyl ether, diphenyl ether, tetrahydrofuran and combinations thereof.

11. The process of claim 1 wherein the mole ratio of a compound of formula II to formaldehyde is in the range from about 0.9:1 to about 1.1:1.

12. The process of claim 1 wherein the mole ratio of a compound of formula I to magnesium alkoxide is in the range from about 2.5:1 to about 3:1.

13. A process for making an oxime of the formula IV

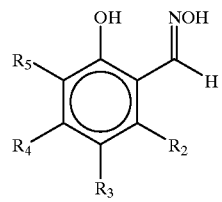

IV wherein each of $R_2$, $R_4$, and $R_5$ is hydrogen and $R_3$ is nonyl which comprises the steps of: (1) reacting a compound of the formula I

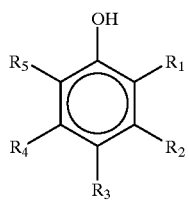

I wherein each of $R_1$, $R_2$, $R_4$ and $R_5$ is hydrogen and $R_3$ is nonyl with magnesium alkoxide to form an aryloxy magnesium compound; (2) reacting the aryloxy magnesium compound with acetic acid to form a compound of the formula II

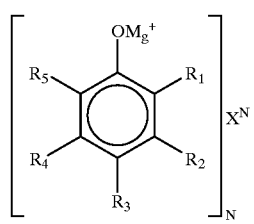

II wherein $R_1$–$R_5$ are defined as above; N is 1 and X is acetate; (3) reacting the aryloxy magnesium salt of the formula II as defined above with formaldehyde to yield an aldehyde of the formula III

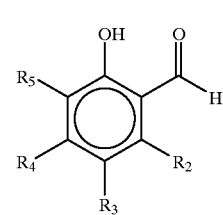

III wherein $R_2$–$R_5$ are defined above; and (4) reacting the aldehyde of formula III with hydroxylamine to produce the oxime of formula IV.

14. The process of claim 13 wherein the mole ratio of a compound of formula II to formaldehyde is in the range from about 0.9:1 to about 1.1:1.

15. The process of claim 13 wherein the mole ratio of a compound of formula I to magnesium alkoxide is in the range from about 2.5:1 to about 3:1.

16. A process for making an aryloxy magnesium salt of the formula II

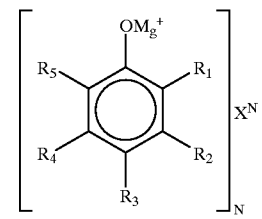

II wherein each of $R_1$–$R_5$ is independently hydrogen, a halogen, an alkyl or cycloalkyl group having from 1 to 36 carbon atoms, an aryl or alkaryl group having from 1 to 36 carbon atoms, an alkoxy or an aryloxy group having from 1 to 30 carbon atoms, an acyl group having from 1 to 24 carbon atoms; X is a non-aryloxy anion selected from the group consisting of chloride, acetate, sulfate, nitrate, sultonate, hydroxide, oxide, carboxylate, and formate; N is an integer having a value of 1 or 2 which comprises the steps of: (1) reacting a compound of the formula I

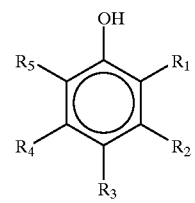

I wherein each of $R_1$–$R_5$ is defined as above with magnesium alkoxide to form an aryloxy magnesium compound; (2) reacting the aryloxy magnesium compound with a compound capable of forming a non-aryloxy anion X to form the aryloxy magnesium salt of formula II.

17. The process of claim 16 wherein $R_3$ is a dodecyl group.

18. The process of claim 16 wherein $R_3$ is a nonyl group.

19. The process of claim 16 wherein $R_3$ is a dodecyl group and each $R_2$, $R_4$, and $R_5$ is hydrogen.

20. The process of claim 16 wherein $R_3$ is a nonyl group and each of $R_2$, $R_4$, and $R_5$ is hydrogen.

21. The process of claim 16 wherein X is an acetate ion.

22. An aryloxy magnesium salt of the formula II

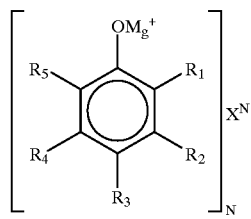

wherein each of $R_1$–$R_5$ is independently hydrogen, a halogen, an alkyl or cycloalkyl group having from 1 to 36 carbon atoms, an aryl or alkaryl group having from 1 to 36 carbon atoms, an alkoxy or an aryloxy group having from 1 to 30 carbon atoms, an acyl group having from 1 to 24 carbon atoms; X is non-aryloxy anion selected from the group consisting of acetate, sulfate, nitrate, sulfonate, hydroxide, oxide, carboxylate, and formate; and N is an integer having a value of 1 or 2.

23. The process of claim 16 wherein $R_3$ is a dodecyl group.

24. The process of claim 16 wherein $R_3$ is a nonyl group.

25. The process of claim wherein $R_3$ is a dodecyl group and each of $R_2$, $R_4$, and $R_5$ is hydrogen.

26. The process of claim 16 wherein $R_3$ is a nonyl group and each of $R_2$, $R_4$, and $R_5$ is hydrogen.

27. A process for making an aldehyde of the formula III

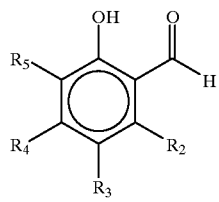

wherein each of $R_2$–$R_5$ is independently hydrogen, a halogen, an alkyl or cycloalkyl group having from 1 to 36 carbon atoms, an aryl or alkaryl group having from 1 to 36 carbon atoms, an alkoxy or an aryloxy group having from 1 to 30 carbon atoms, or an acyl group having from 1 to 24 carbon atoms which comprises the steps of: (1) reacting a compound of the formula I

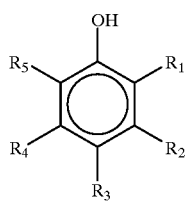

wherein each of $R_2$–$R_5$ is defined as above and with the proviso that one of $R_1$ or $R_5$ is hydrogen with magnesium alkoxide to form an aryloxy magnesium compound; (2) reacting the aryloxy magnesium compound with a compound capable of forming a non-aryloxy anion X wherein X is selected from the group consisting of acetate, sulfate, nitrate, sulfonate, hydroxide, oxide, carboxylate and formate to form an aryloxy magnesium salt of the formula II

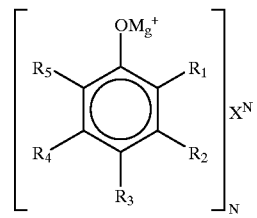

wherein $R_1$–$R_5$, and X are defined as above; and N is an integer having a value of 1 or 2; and (3) reacting the aryloxy magnesium salt of the formula II with formaldehyde to yield an aldehyde of formula III.

28. The process of claim 27 wherein in formula I $R_3$ is a dodecyl group.

29. The process of claim 27 wherein in formula I $R_3$ is a nonyl group.

30. The process of claim 27 wherein in formula I $R_3$ is a dodecyl group and each of $R_2$, $R_4$ and $R_5$ is hydrogen.

31. The process of claim 27 wherein in formula I $R_3$ is a nonyl group and each of $R_2$, $R_4$ and $R_5$ is hydrogen.

32. The process of claim 27 wherein in formula II X is an acetate ion.

33. The process of claim 27 wherein step (1) is carried out in the presence of a non-polar solvent.

34. The process of claim 33 wherein the non-polar solvent is one or more of the solvents selected from the group consisting of benzene, toluene, xylene and cyclohexane.

35. A process according to claim 33 wherein a polar co-solvent is used in conjunction with the non-polar solvent.

36. A process according to claim 35 wherein the polar co-solvent is selected from the group consisting of methanol, ethanol, triethylamine, pyridine, dimethylformamide, N,N-dimethylacetamide, dimethyl sulfoxide, mono-glyme, di-glyme, tri-glyme, diethyl ether, diphenyl ether, tetrahydrofuran and combinations thereof.

37. The process of claim 36 wherein the mole ratio of a compound of formula II to formaldehyde is in the range from about 0.9:1 to about 1.1:1.

38. The process of claim 36 wherein the mole ratio of a compound of formula I to magnesium alkoxide is in the range from about 2.5:1 to about 3:1.

39. A process for making an aldehyde of the formula III

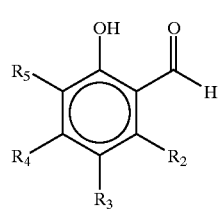

wherein each of $R_2$, $R_4$ and $R_5$ is hydrogen and $R_3$ is nonyl which comprises the steps of: (1) reacting a compound of the formula I

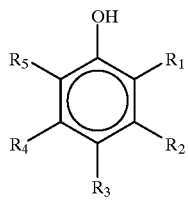

I wherein each of $R_1$, $R_2$, $R_4$ and $R_5$ is hydrogen and $R_3$ is nonyl with magnesium alkoxide to form an aryloxy magnesium compound; (2) reacting the aryloxy magnesium compound with acetic acid to form a compound of formula II

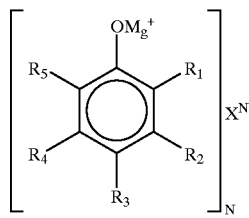

II wherein $R_1$–$R_5$ are defined as above; N is 1 and X is acetate; (3) reacting the aryloxy magnesium salt of the formula II as defined above with formaldehyde to yield an aldehyde of the formula III.

40. The process of claim 39 wherein the mole ratio of a compound of formula II to formaldehyde is in the range from about 0.9:1 to about 1.1:1.

41. The process of claim 39 wherein the mole ratio of a compound of formula I to magnesium alkoxide is in the range from about 2.5:1 to about 3:1.

42. The process of claim wherein step (3) is carried out in the presence of water.

* * * * *